(12) United States Patent
Laufer et al.

(10) Patent No.: US 10,773,069 B2
(45) Date of Patent: *Sep. 15, 2020

(54) MEDICAL DEVICES AND METHODS FOR FLUID TRANSFER

(71) Applicants: Michael D. Laufer, Menlo Park, CA (US); Gary Yip, San Carlos, CA (US)

(72) Inventors: Michael D. Laufer, Menlo Park, CA (US); Gary Yip, San Carlos, CA (US)

( * ) Notice: Subject to any disclaimer, the term of this patent is extended or adjusted under 35 U.S.C. 154(b) by 167 days.

This patent is subject to a terminal disclaimer.

(21) Appl. No.: 15/901,553

(22) Filed: Feb. 21, 2018

(65) Prior Publication Data

US 2018/0177995 A1 Jun. 28, 2018

Related U.S. Application Data

(63) Continuation of application No. 14/702,373, filed on May 1, 2015, now Pat. No. 9,907,945.

(60) Provisional application No. 61/987,330, filed on May 1, 2014.

(51) Int. Cl.
*A61M 39/22* (2006.01)

(52) U.S. Cl.
CPC ....... *A61M 39/22* (2013.01); *A61M 2039/224* (2013.01); *A61M 2039/229* (2013.01); *A61M 2205/581* (2013.01); *A61M 2205/582* (2013.01)

(58) Field of Classification Search
CPC .......... A61M 39/26; A61M 2039/2486; A61M 2039/268; A61M 2039/224; A61M 5/16813
See application file for complete search history.

(56) References Cited

U.S. PATENT DOCUMENTS

| | | |
|---|---|---|
| 5,443,453 A | 8/1995 | Walker et al. |
| 6,874,664 B1 | 4/2005 | Montgomery et al. |
| 7,152,845 B2 | 12/2006 | Carrez et al. |
| 7,914,495 B2 | 3/2011 | Amor et al. |
| 2006/0129109 A1 | 6/2006 | Shaw et al. |
| 2007/0017583 A1 | 1/2007 | Fangrow, Jr. et al. |
| 2008/0185056 A1 | 8/2008 | Diodati et al. |
| 2014/0303601 A1 | 10/2014 | Fangrow et al. |

*Primary Examiner* — Emily L Schmidt (74) *Attorney, Agent, or Firm* — Convergence Intellectual Property Law P.C.; Johnathan Garfinkel (57) ABSTRACT

Fluid flow control devices for medical use are disclosed. On one end, a fluid flow control device is configured to be attached to a manifold that is in-line with an infusion setup and the other end of the fluid flow control device is configured to be attached to a sampling or infusion device, such as a syringe. In one aspect, a fluid flow control device has an external casing and an internal casing which is configured to be movably housed within the external casing. The internal casing mates with a fluid outlet on the external casing and upon separating the internal and external casings a fluid flow path is established.

20 Claims, 8 Drawing Sheets

MEDICAL DEVICES AND METHODS FOR FLUID TRANSFER

This application is a continuation of U.S. patent application Ser. No. 14/702,373, filed May 1, 2015, which claims the benefit and priority of U.S. Provisional Application No. 61/987,330, filed on May 1, 2014, the full disclosures of the above referenced applications are incorporated herein by reference.

FIELD OF THE INVENTION

Aspects of the present disclosure relate generally to medical devices and methods for fluid transfer, and more particularly, relate to a fluid flow control device that connects a medical fluid source to a patient.

BACKGROUND

In the medical field, it is often necessary to manipulate fluid flow through conduits by opening, closing and diverting fluid flow to transport or mix fluids from various sources. The most common example of this occurs in medicine where a fluid transfer line such as an intra-arterial line, intravenous line, or intrathecal line, etc. is used to either infuse medicament (medication and/or fluid) into a patient or draw fluids (blood for testing) from the patient. Often, a single intravenous line will need to be the simultaneous port for both withdrawal and introduction of multiple fluids.

A common way to accomplish this is through the use of medical stopcocks which are most commonly of the "3 way type" or less commonly "4 way type". These inventions allow ports to be opened or closed as need be to allow or disallow the flow of a given medicament or to allow direct access to the fluid system for the above stated reasons. Often they may require several hands to simultaneously manipulate the valve and a syringe or another connected device. Such devices are described in U.S. Pat. Nos. 7,914,495, 7,152,845, 5,443,453, and 6,874,664.

A common problem with the use of these medical stopcocks is that during use, they often allow an open pathway into the vessel or bodily space, which increases the risk for contamination. For example, in one of the embodiments described above, the cap may be taken off the stopcock valve and be placed on an unclean surface before being replaced onto the stopcock. Such an action would clearly subject the port, and thereby the intravenous device and the patient, to contamination. In order to aid in sterility, ease of use and efficiency, improvements are needed.

SUMMARY

Disclosed herein are fluid flow control devices and methods for medical use. In one aspect, the fluid flow control device comprises an external casing comprising first and second openings, and an internal casing which is configured to be movably housed within the external casing. In one aspect, the internal casing comprises a locking mechanism to lock a part of the external casing, and a base attached to the internal casing, wherein the base is configured to mate with a port of an infusion device.

In one aspect, the fluid flow control device is in a closed position when the internal casing is completely housed within the external casing, and the fluid flow control device is in an open position when the internal casing is not completely housed within the external casing. The internal casing comprises at least one orifice that is separate from the opening of the external casing. The opening of the internal casing is configured to be removably attached to an infusion device.

In one aspect, the fluid flow control device comprises several additional features. In one aspect, the locking mechanism of the fluid flow control device comprises a notch, a groove or a clip. Further, the medical device used in conjunction with the fluid flow control device may be an intravenous cannula or a device attachable to an intravenous cannula. Further, in one aspect, the openings of the external casing are configured to facilitate movement of a fluid, and the opening of the internal casing is configured to maintain sterility while receiving a needle, for example, by comprising a septum. In one aspect, the fluid flow control device further comprises a feedback mechanism to alert the user when the fluid flow control device is in a sufficiently open position. In one aspect, the feedback mechanism is a tactile feedback mechanism or an auditory feedback mechanism, or a visual feedback system. Further, in another aspect, the base is configured to mate with a port of an external device via a luer lock. Additionally, in yet another aspect, the device further comprises a blocking mechanism disposed on the internal casing configured to block a fluid path from the opening of the external casing.

Also disclosed are alternative embodiments to the above, wherein the external casing comprises the base attachable to the infusion device. Also disclosed are methods of using the above devices.

These and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

FIG. 2b shows one perspective view of the top portion of device as shown in FIG. 2a.

FIG. 2c shows another perspective view of the top portion of device as shown in FIG. 2a.

FIG. 2d shows yet another perspective views of the top portion of device as shown in FIG. 2a.

DETAILED DESCRIPTION

Although the detailed description contains many specifics, these should not be construed as limiting the scope of the disclosure but merely as illustrating different examples and aspects of the disclosure. It should be appreciated that the scope of the disclosure includes other aspects and embodiments not discussed herein. Various other modifications, changes and variations which will be apparent to those skilled in the art may be made in the arrangement, operation and details of the method, device, and system of the aspects and embodiments disclosed herein without departing from the spirit and scope of the disclosure as described here.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The disclosure describes a fluid flow control device configured to mate with medical fluid flow devices such as intravenous devices, intra-arterial devices, intrathecal devices, etc, including manifolds that connect medical fluid sources and a patient. Though intravenous devices are provided as a convenient example, it should be understood that other devices facilitating medical fluid exchange (for example, intra-arterial, intrathecal devices, etc.), may be similarly used in conjunction with aspects of the disclosure. In one embodiment, the fluid flow control valve comprises an external casing and an internal casing, either of which comprises a base that is configured to mate with the intravenous device. The external casing comprises a first and second opening. The internal casing is movably housed within the external casing and contains a locking mechanism to lock a part of the external casing and a blocking mechanism that blocks fluid from flowing through an opening of the external casing.

In some aspects, the valve is in a closed position when the internal casing is fully housed within the external casing. To open the valve and allow fluid flow through the device, a user separates the external casing and the internal casing such as by pulling apart the external casing and the internal casing. One end of the valve is configured to mate with a fluid exchange device, e.g., an intravenous device, while the other end of the valve is configured to receive a device such as a syringe that is used to either remove or introduce fluids via the valve.

Figure 1:
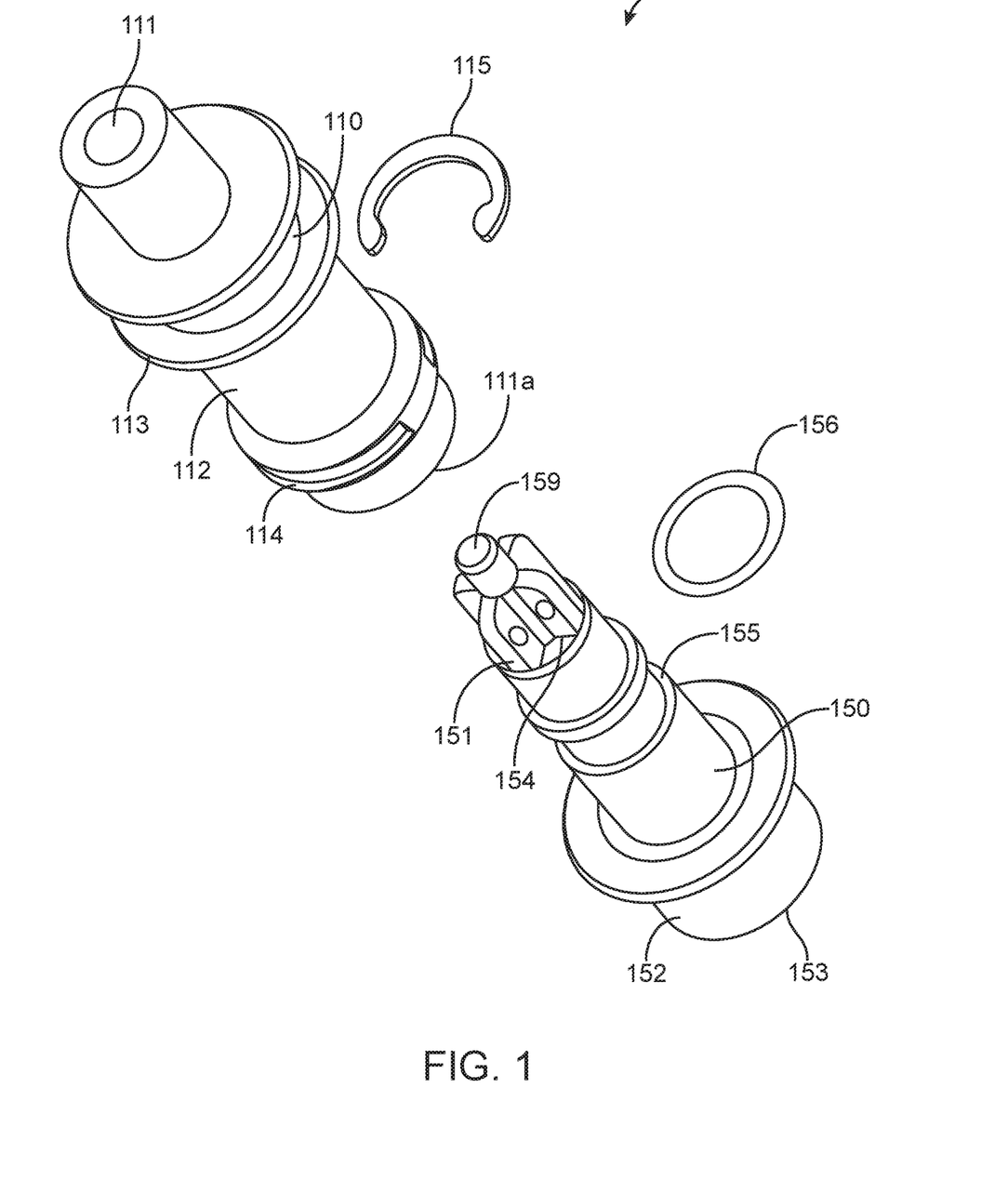
FIG. 1 shows a perspective view of the fluid flow control device in accordance with one embodiment of the present invention.

With reference to the figures, FIG. 1 describes an embodiment of the fluid flow control device 100. The fluid flow control device (hereinafter also referred to as "device 100") comprises an external casing 110 (hereinafter also referred to as "external casing" or "casing 110") and an internal casing 150 (hereinafter also referred to as "internal casing" or "casing 150"). In one embodiment, both external and internal casings 110 and 150 are described as being cylindrical or tubular. However, the casings may take on any shape, such as rectangular, ovoid, etc. External casing 110 comprises a hollow body with a first opening 111, and a second opening 111a. Additionally and optionally, casing 110 comprises elements that facilitate a user to easily grip the device, such as one or more rims 113, and indentations 112 found in the spaces between the rims. Additionally and optionally, the device comprises a locking mechanism 115 configured to prevent accidental separation of the casings 110 and 150 of the device 100. In the present embodiment, the locking mechanism 115 is configured as a locking clip that is configured to be received in groove 114. Groove 114 is configured to correspond to a part of the internal casing 150 in a manner that prevents movement of casing 150 in relation to casing 110. The locking mechanism 115 also prevents the complete separation of external casing 110 and internal casing 150, described in detail below, during the operation of the device.

Internal casing 150 comprises a hollow cylindrical body terminating in a fluid port 151 at one end and a base 152 at the other end. Fluid port 151 comprises one or more orifices 154 that are separate from opening 111a of the external casing. Base 152 comprises an opening 153 that is configured to mate with another device, such as an intravenous device, for example via grooves 114 appropriate for a luer lock. Additionally, internal casing 150 comprises a sealing mechanism 156 that is configured to create a seal in the space between the external casing 110 and internal casing 150 and thus prevent leakage of fluid from the device. In one embodiment, the sealing mechanism 156 is configured as sealing ring, which fits around some part of the cylindrical body 155 of internal casing 150. Additionally and optionally, casing 150 comprises blocking tip 159, which is configured to prevent fluid leaking from the opening of the external casing when the blocking tip 159 is engaged with the external casing 110 in a manner that blocks opening 111.

In one embodiment, base 152 is shown as being part of the internal casing, and the opening 111 is shown as being part of the external casing 110. However, alternative embodiments may exist where the external casing comprises the base 152 that mates with the intravenous device and the internal casing 150 comprises an opening 111 to receive a syringe.

Figure 2A:
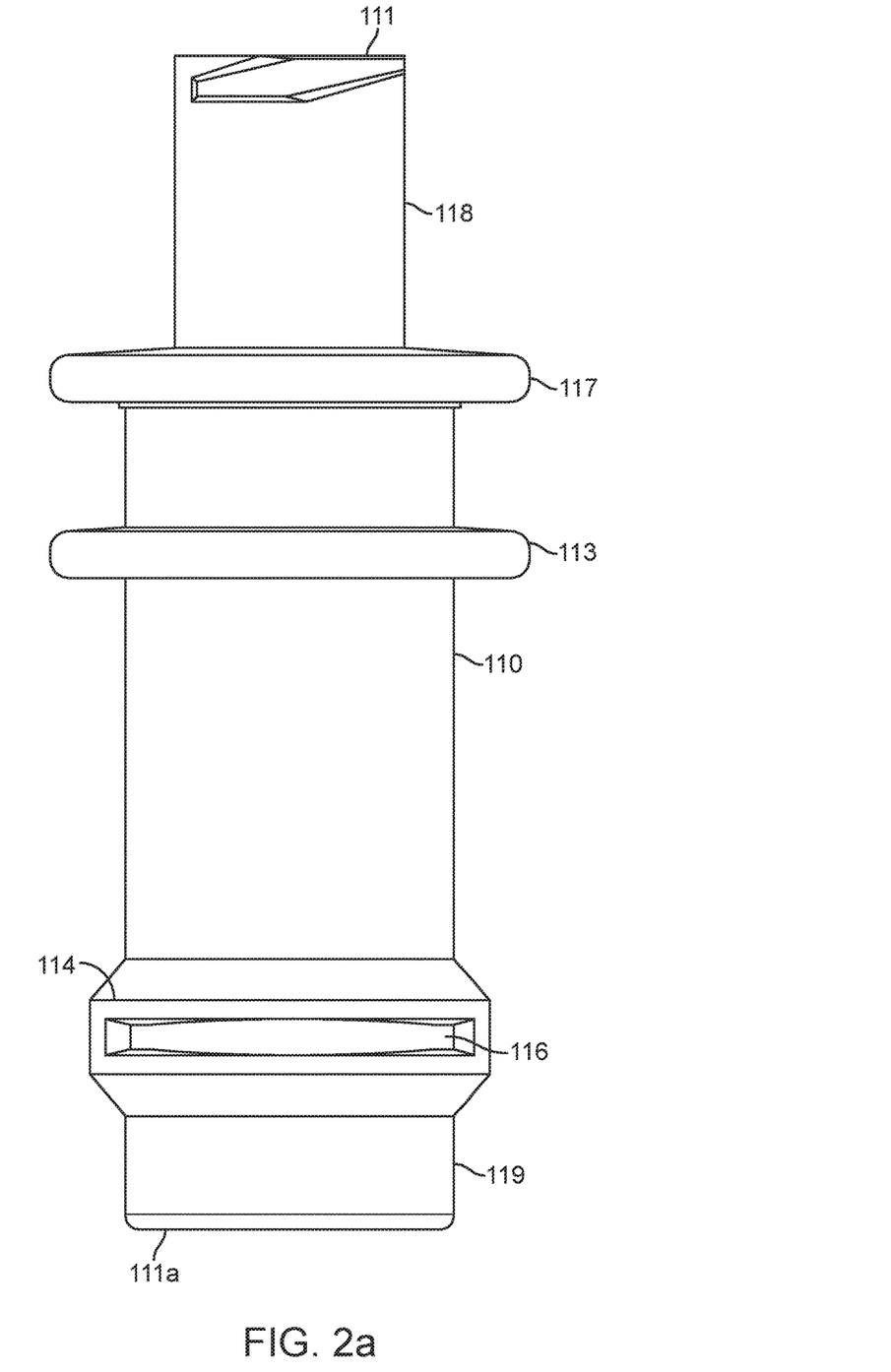
FIG. 2a shows a perspective view of one portion of the fluid flow control device shown in FIG. 1.

FIG. 2a shows the external casing in greater detail. As previously mentioned, external casing 110 comprises a first opening 111, and a second opening 111a. In the present embodiment, the first opening 111 is shown as being configured to mate with another device, such as an intravenous device, (including a manifold associated with such a device) via a narrowing of the cylindrical body in sub-portion 118. However, alternative embodiments may exist whereby the first opening 111 is not housed in a sub-portion that is narrower than the remainder of the external casing 110. For example, the first opening 111 may be housed in a sub-portion that either narrows or widens in relation to the rest of the external casing 110.

Figure 2B:
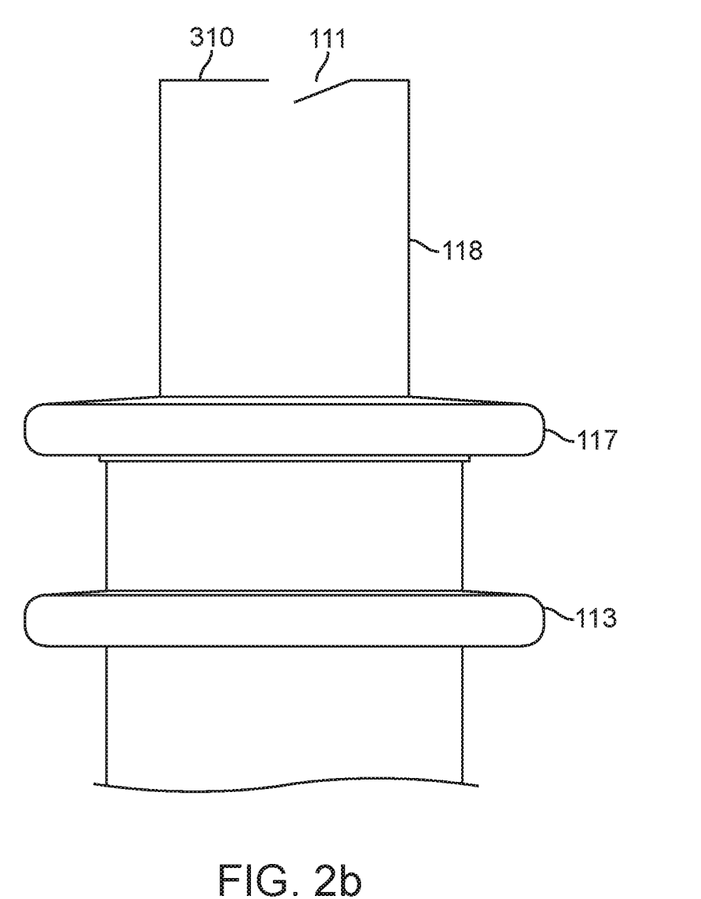

Additionally, there may be additional features to aid in ensuring sterility of fluid transfer. For example, as seen in FIG. 2b, the opening 111 of the external casing 110 is optionally configured to maintain sterility while receiving a needle or a portion of an external device such as a luer hub. In some aspects, one embodiment of the present disclosure comprises a septum or other membrane 310 that at least partly covers the opening 111. For example, in one embodiment, the membrane 310 may cover a portion of the opening 111 while maintaining an access channel to allow an external device to perform fluid transfer via the access channel. In other aspects, one embodiment comprises a septum or other membrane that completely covers the opening 111. For example, in one embodiment, the septum is configured to substantially completely cover the opening 111, where the septum is capable of being pierced by the needle to initiate fluid transfer.

Figure 2C:
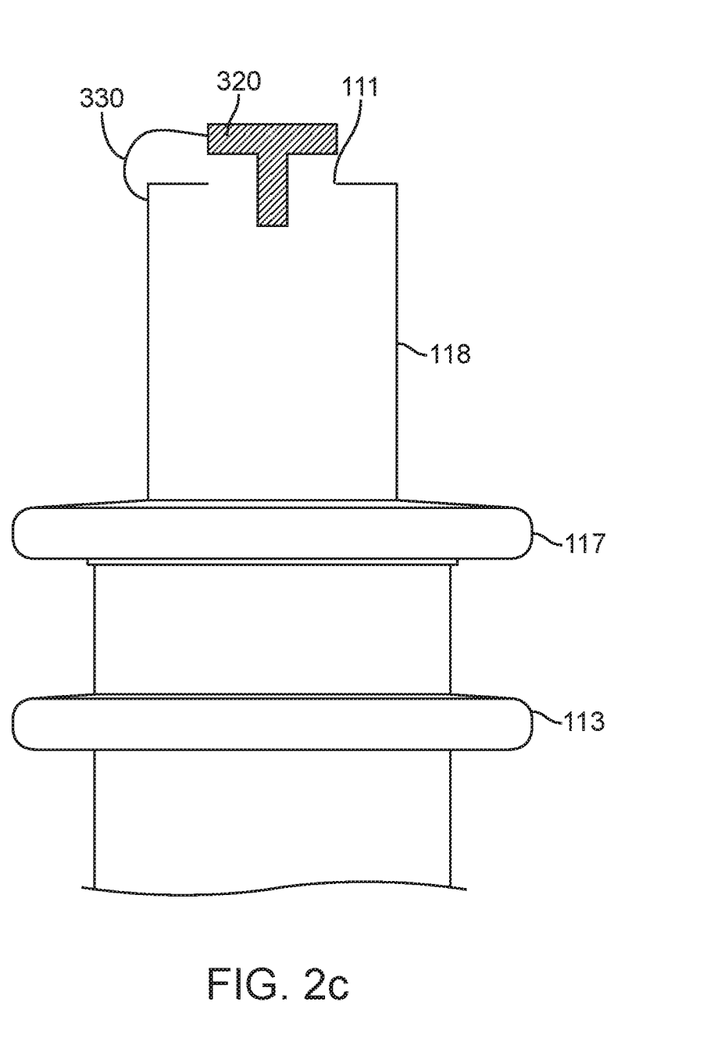
Figure 2D:
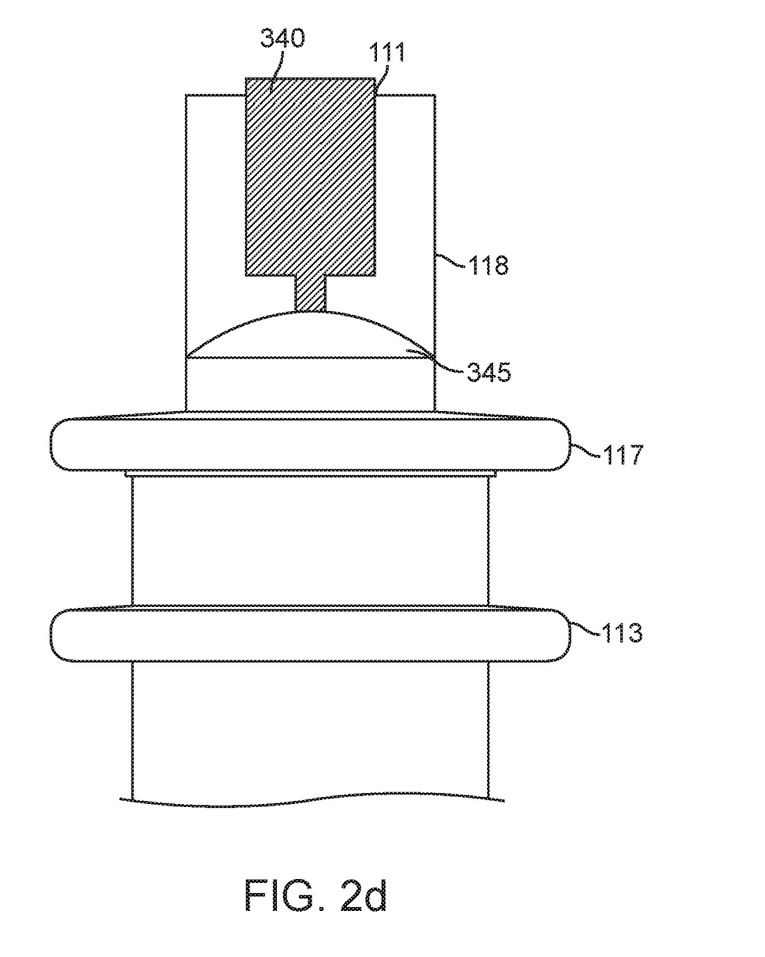

Further, as seen in FIG. 2c, a cap 320 may be provided to cover the opening 111. The cap 320 is optionally tethered to the device 100 via tether 330, and is removed prior to using the device 100. In some aspects, the tether 330 is a string that functions as a harness that is either removably or permanently attached to the cap 320 and the device 100. As shown in FIG. 2d, a plunger 340 can be provided within an opening of the device 100. The plunger 340 is arranged so as to cover the opening until usage, when the plunger 340 is removed.

Optionally, the movement of the plunger 340 is facilitated or automated by a mechanism 345. In one embodiment, the mechanism 345 is configured as a spring, which is compressed prior to the use of the device 100. Upon usage of the device 100, i.e., when then springe is attached, the spring 345 is decompressed, thereby pushing the plunger 340 out of the opening 111. In another embodiment, the mechanism 345 is configured as a piston mechanism.

Additionally, opening 111a is configured to house at least a portion of the movable internal casing (not shown). Thus, in one embodiment, opening 111a is contained in a sub-portion 119 of the cylindrical body that is of the same diameter as the rest of the external casing 110, and a larger diameter than at least a portion of the internal casing 150. However, alternative embodiments may exist whereby the opening 111a is not housed in a sub-portion 119 that is of the same diameter as the rest of the external casing 110. For example, opening 111a may be housed in a sub-portion 119 that either narrows or widens in relation to the rest of the external casing 110.

Additionally and optionally, casing 110 comprises elements that facilitate a user's grip on the device 100, such as one or more indentations 112 shown in FIG. 1, and/or one or more rims 113, 117 shown in FIG. 2a. Optionally, the device comprises a locking mechanism 115 to prevent casings 110 and 150 from separating completely. In the resting state of device 100, the external casing 100 houses a significant portion of the internal casing 150. To open the device 100, a user separates the external and internal casings 110 and 150, for example, by pulling apart the external and internal casings 110 and 150. The locking mechanism ensures that the casings 110 and 150 are not fully disengaged. Thus, the locking mechanism prevents accidental separation of the two casings 110 and 150 of the device. In the present embodiment, the locking mechanism 115 is locking clip shown in FIG. 1 that is configured to be received in groove 114, which contains opening 116 as seen in FIG. 2 to receive the clip 115. Though the present embodiment shows a clip 115, alternative embodiments may exists where the locking mechanism comprises a groove or notch 114 on the external casing 110 that corresponds to a groove or notch 114 on the internal casing 150.

Figure 3:
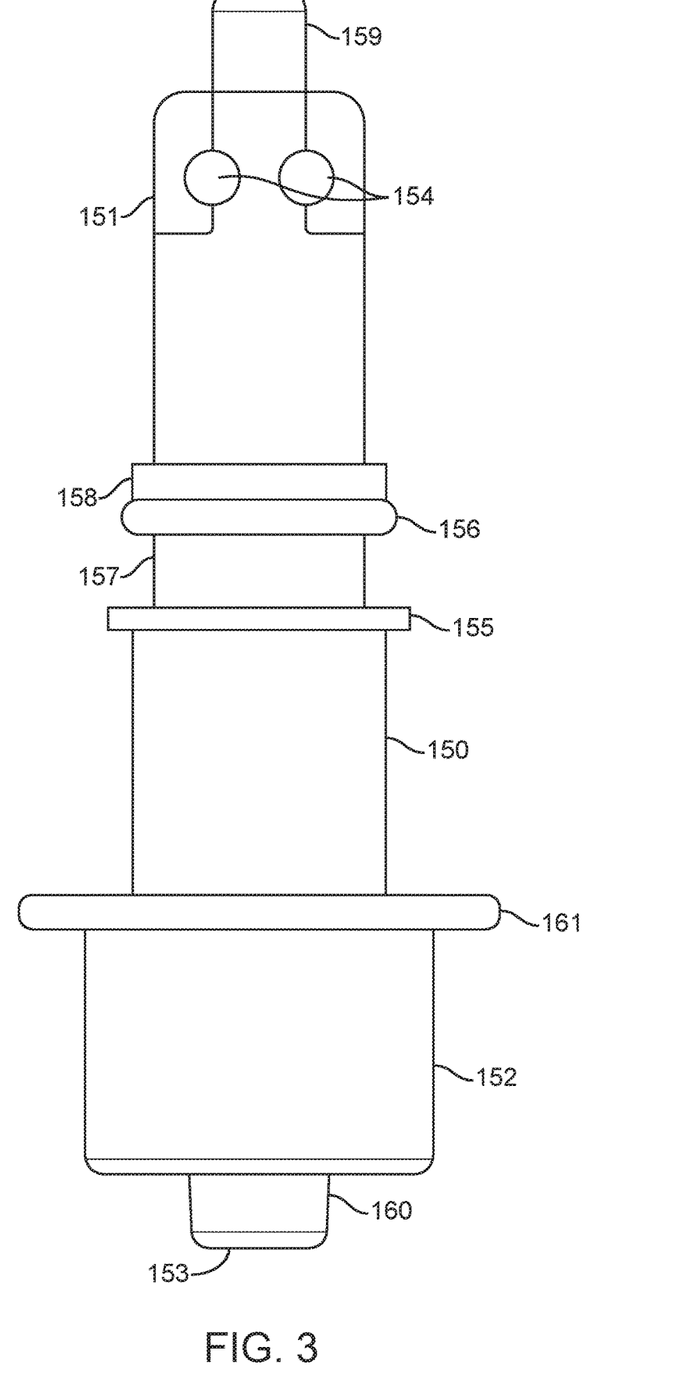
FIG. 3 shows a perspective view of another portion of the fluid flow control device shown in FIG. 1.

FIG. 3 shows a detailed view of the internal casing 150. Casing 150 comprises a hollow cylindrical body, comprising a fluid conduit shown in FIG. 5 as 170. One end of the fluid conduit 170 comprises fluid port 151, which contains at least one orifice 154, and the opposite end of the fluid conduit 170 comprises opening 153. Orifices 154 are placed such that they are in fluid continuity with opening 153. The opposite end of casing 150 comprises a base 152, which is configured to mate with a fluid infusion or sampling device, such as a syringe. Base 152 contains one or more features to assist in usage, for example a holdably wide sub-portion 161. Base 152 terminates in an opening 153 that is optionally housed in basal rim 160. Basal rim 160 is shown in this embodiment as protruding from the remainder of the internal casing 150. However, the opening of base 152 may exists without such a basal rim 160.

Additionally, the internal casing 150 comprises a sealing mechanism to prevent leakage of fluid from the device 100. In this embodiment, the sealing mechanism is shown as a sealing ring 156 which surrounds an outer perimeter of the internal casing 150. The sealing ring's 156 sealing properties may be enhanced by the presence of a groove 157, and first and second notches 155 and 158. Notch 155 is located below the sealing ring 156 and notch 158 is located above the sealing ring 156. As shown in this embodiment, the sealing ring 156 movably resides in the groove 157, and its movement is limited on either side by notches 155 and 158. However, alternative embodiments may exists where the sealing ring 156 resides on the body independent of a notch 158 or groove 157. The sealing ring 156 is configured such that when casing 150 resides within casing 110, the sealing ring 156 touches the internal wall of casing 110, thereby preventing leakage of fluid. The ring 156 may also act as an eccentric spring, that when rolled, provides a snap resulting in a tactile and/or auditory feedback of the opening and/or closing of the device.

Optionally, in some aspects, the internal casing 150 comprises one or more features to aid a user in holding the device 100. For example, casing 150 may comprise a holding rim 161.

Figure 4:
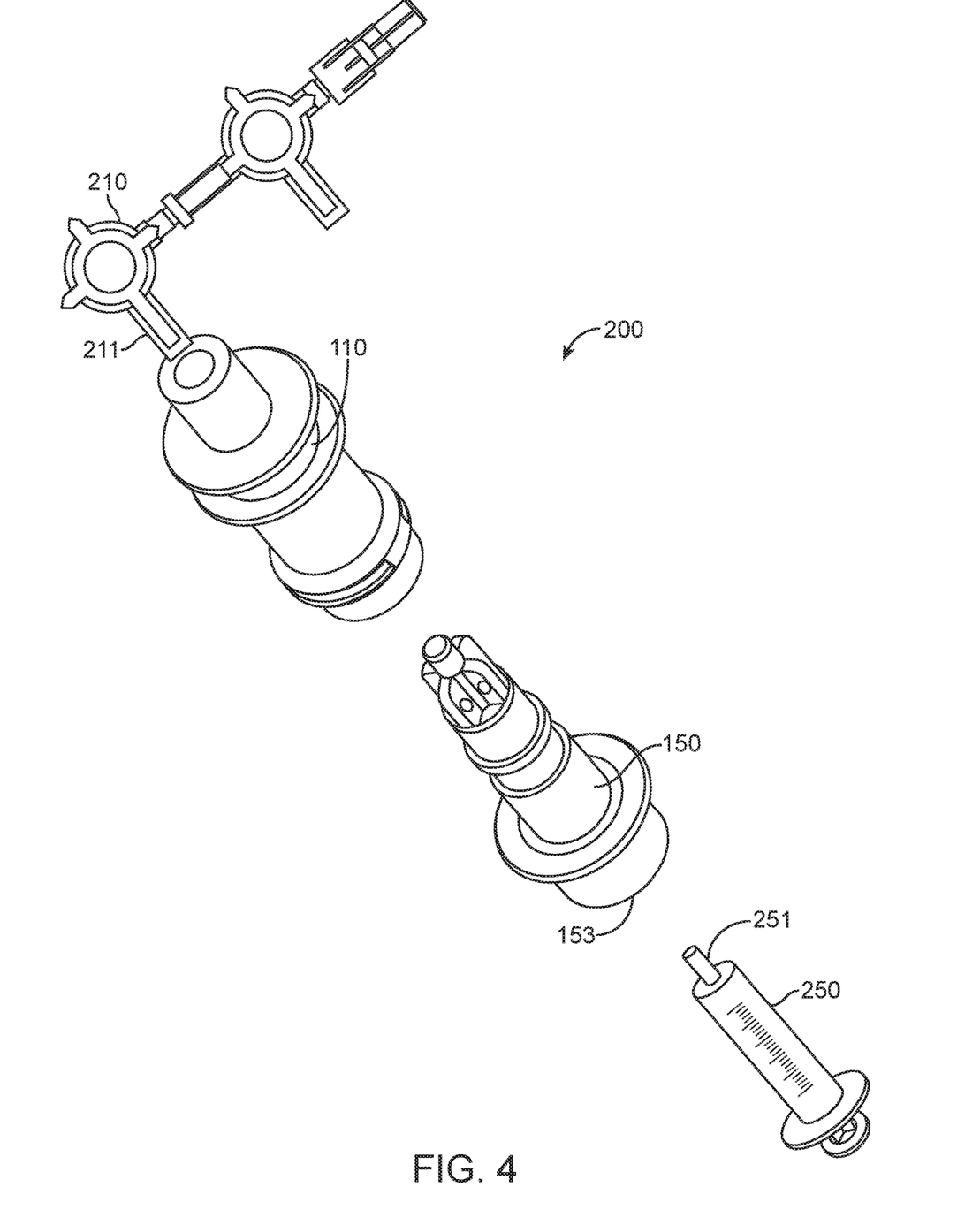
FIG. 4 shows a perspective view of a system incorporating the fluid flow control device shown in FIG. 1.

FIG. 4 shows a system incorporating the device shown in FIG. 1 to FIG. 3. In some aspects, the device 100 is connectable to a manifold 210 that is in-line with an intravenous device and a fluid exchange device 250, such as a syringe. Though an intravenous device is provided as a convenient example, it should be understood that any other device facilitating medical fluid exchange (for example an intra-arterial device, intrathecal device, etc.), may be similarly used in conjunction with the described invention. Additionally, though shown as removable in this embodiment, one end of the device can also be integrally connected or incorporated with a manifold. For example, in one embodiment, one end of the device as described herein may be molded with a manifold. Further, in some aspects, there can be two or more of the devices each connected (removably or integrally) to an access port of the manifold.

As shown in FIG. 4, the external casing 110 is connected to the device 210 (in this case a stop-cock manifold) in such a manner that an intravenous port 211 of the intravenous device mates with the opening of the external casing 110. It should be noted that the intravenous device may be an intravenous cannula, or, as shown in FIG. 4, may be a device attachable to an intravenous cannula.

Further, the internal casing 150 is configured to connect with fluid transfer device 250 (in this case, a syringe), such that the infusion port 251 of the syringe mates with the opening 153 of the internal casing 150. Additionally, there may be additional features to aid in ensuring sterility of fluid transfer. For example, the same features shown in FIG. 2b through FIG. 2d may be used for opening 153. So, for example, as seen in FIG. 2b, the opening of the internal casing 150 is optionally configured to maintain sterility while receiving a needle, for example by comprising a septum or other membrane 310 that at least partly covers the opening. Further, as seen in FIG. 2c, a cap 320 may be provided to cover the opening. The cap is optionally tethered to the device via tether 330, and is removed prior to using the device. As shown in FIG. 2d, a plunger 340 can be provided within an opening of the device. The plunger 340 is arranged so as to cover the opening until usage, when the plunger 340 is removed. Optionally, the movement of the plunger 340 is facilitated or automated by a spring 345, which is compressed prior to the use of the device 100. Upon usage of the device 100, the spring 345 is decompressed, thereby pushing the plunger 340 out of the opening.

Though the embodiment above shows the intravenous device 210 being attachable to the external casing 110 and the infusion device being attachable to the internal casing 150, alternative embodiments are possible where the intravenous device 210 would be attachable to the internal casing 150 and the syringe 250 would be attachable to the external casing 110.

In practice, one end of the device 100 would be attached to the intravenous device 210. Optimally, the device 100 is in a closed position to ensure sterility. The device 100 is configured to be either permanently or temporarily attached to the intravenous device 210. The syringe 250 is then attached to the other end of the device 100. The device 100 is then opened to allow for an open fluid path through the device 100. Opening occurs by pulling the external casing 110 away from the internal casing 150. Fluid exchange is thereafter affected through the syringe, either by drawing or introducing fluids via the device 100. The fluid path through the device 100 can thus be in either direction.

Figure 5:
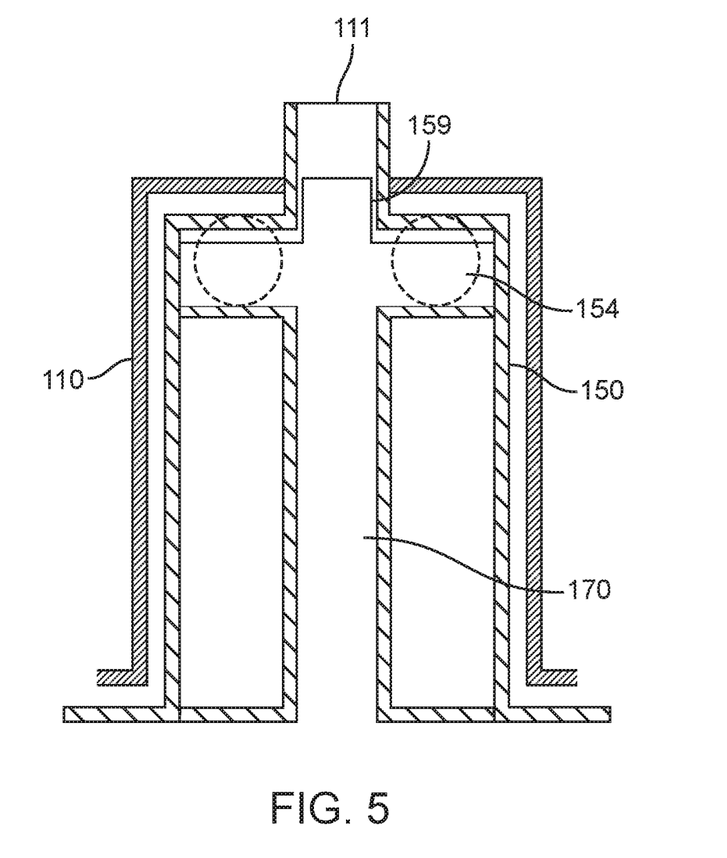
FIG. 5 shows a perspective of the internal structure of the fluid flow control device in a closed position.

Fluid flows through the device from an opening at one end, through the orifices 154 and then to the opening at the other end. Fluid flow is controlled via the orifices 154 on the internal casing 150, which are separate from the openings 111 and 111a of the external casing 110. When in the closed position, the external casing 110 houses the internal casing 150 such that orifices 154 are covered by the internal wall of the external casing 110 (as seen in FIG. 5). Simultaneously, in the closed position, the opening 111 on the external casing 110 is blocked by the tip 159 of the casing 150.

When in the open position, the external casing 110 is pulled away from the internal casing 150 such that the orifices 154, as well as the opening 111a on the external casing 110 are uncovered. Fluid is thus allowed to flow in either direction between opening 111 of the device through and opening 153 via the orifices 154.

Additionally, the device may comprise a feedback mechanism (not shown) to alert the user when the device is in a sufficiently open position. Such a mechanism may be a tactile feedback mechanism (for example, feeling resistance to movement) or an auditory feedback mechanism (for example, a click).

Although the disclosure describes using a device to aid in sterile intravenous fluid transfer, it is contemplated that various aspects of the present disclosure described herein may be applied to various other therapeutic or cosmetic operations.

In addition to above-mentioned components, the subject systems or kits comprising the described systems typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A fluid flow control device for medical use, the device comprising:
   an external casing comprising an opening;
   an internal casing comprising an opening configured to attach to a fluid transfer device, wherein the internal casing is configured to be movably housed within the external casing; and
   a locking mechanism configured to prevent separation of the internal and external casings, wherein the locking mechanism comprises a locking clip configured to be separable from the external and internal casings by sliding the locking clip orthogonal to a longitudinal axis of the device; and
   a base attached to the external casing, wherein the base is configured to mate with a port of an intravenous device, intra-arterial device, or intrathecal device; and
   wherein the fluid flow control device is in a closed position when the internal casing is completely housed within the external casing, and the fluid flow control device is in an open position when the internal casing is not completely housed within the external casing; and
   wherein the external casing further comprises a groove having an opening configured to lead to a part of the internal casing; and wherein the locking clip is configured to be received in the opening by sliding the locking clip orthogonal to the longitudinal axis of the device thereby limiting longitudinal movement of the internal casing in relation to the external casing to prevent the internal and external casings from separating completely while allowing limited longitudinal movement to transition the device from the closed position to the open position and from the open position to the closed position.

2. The device of claim 1, wherein the internal casing comprises at least one orifice that is separate from the opening of the external casing; wherein the at least one orifice is covered by an internal wall of the external casing when the device is in the closed position.

3. The device of claim 1, wherein the device additionally comprises a sealing mechanism configured to create a seal in a space between the external casing and the internal casing and prevent leakage of fluid from the device.

4. The device of claim 1, wherein the opening of the external casing is configured to facilitate movement of a fluid.

5. The device of claim 1, wherein the fluid flow control device further comprises a feedback mechanism to alert the user when the fluid flow control device is in a sufficiently open or closed position, wherein the feedback mechanism is an auditory feedback mechanism.

6. The device of claim 1, further comprising a blocking mechanism disposed on the internal casing configured to block a fluid path from the opening of the external casing.

7. A fluid flow control device for medical use, the device comprising:
   an external casing comprising an opening configured to attach to a fluid transfer device;
   an internal casing comprising an opening, wherein the internal casing is configured to be movably housed within the external casing; and
   a locking mechanism configured to prevent separation of the internal and external casings, wherein the locking mechanism comprises a locking clip configured to be separable from the external and internal casings by sliding the locking clip orthogonal to a longitudinal axis of the device; and a base attached to the internal casing, wherein the base is configured to mate with a port of an intravenous device, intra-arterial device, or intrathecal device; and wherein the fluid flow control device is in a closed position when the internal casing is completely housed within the external casing, and the fluid flow control device is in an open position when the internal casing is not completely housed within the external casing; and wherein the external casing further comprises a groove having an opening configured to lead to a part of the internal casing; and wherein the locking clip is configured to be received in the opening by sliding the locking clip orthogonal to the longitudinal axis of the device thereby limiting longitudinal movement of the internal casing in relation to the external casing to prevent the internal and external casings from separating completely while allowing limited longitudinal movement to transition the device from the closed position to the open position and from the open position to the closed position.

8. The device of claim 7, wherein the internal casing comprises at least one orifice that is separate from the opening of the external casing; wherein the at least one orifice is covered by an internal wall of the external casing when the device is in the closed position.

9. The device of claim 7, wherein the device additionally comprises a sealing mechanism configured to create a seal in a space between the external casing and the internal casing and prevent leakage of fluid from the device.

10. The device of claim 7, wherein the opening of the external casing is configured to facilitate movement of a fluid.

11. The device of claim 7, wherein the fluid flow control device further comprises a feedback mechanism to alert the user when the fluid flow control device is in a sufficiently open or closed position, wherein the feedback mechanism is an auditory feedback mechanism.

12. The device of claim 7, further comprising a blocking mechanism disposed on the internal casing configured to block a fluid path from the opening of the external casing.

13. A system incorporating a medical fluid flow control device, the system comprising:
a medical fluid flow control device, wherein the fluid flow control device comprises:
an external casing with an opening;
an internal casing with an opening, wherein the internal casing is configured to be movably housed within the external casing; and
a locking mechanism configured to prevent separation of the internal and external casings, wherein the locking mechanism comprises a locking clip configured to be separable from the external and internal casings by sliding the locking clip orthogonal to a longitudinal axis of the device; and a fluid transfer device comprising a port; and a base attached to the fluid flow control device, wherein the base is configured to mate with the port of the fluid transfer device;

wherein the fluid flow control device is in a closed position when the internal casing is completely housed within the external casing, and the fluid flow control device is in an open position when the internal casing is not completely housed within the external casing; and wherein the external casing further comprises a groove having an opening configured to lead to a part of the internal casing; and wherein the locking clip is configured to be received in the opening by sliding the locking clip orthogonal to the longitudinal axis of the device thereby limiting longitudinal movement of the internal casing in relation to the external casing to prevent the internal and external casings from separating completely while allowing limited longitudinal movement to transition the device from the closed position to the open position and from the open position to the closed position.

14. The system of claim 13, wherein the opening of the internal casing is configured to be removably attached to a port of an intravenous device, intra-arterial device, or intrathecal device; and the base is attached to the external casing.

15. The system of claim 13, wherein the opening of the external casing is configured to be removably attached to a port of an intravenous device, intra-arterial device, or intrathecal device; and the base is attached to the internal casing.

16. The system of claim 13, wherein the base is integrally connected with the port of the fluid flow control device.

17. The system of claim 13, wherein the base removably mates with the port of the fluid flow control device.

18. The system of claim 13, wherein the opening of the external casing is configured to facilitate movement of a fluid.

19. The system of claim 13, wherein the fluid flow control device further comprises a feedback mechanism to alert the user when the fluid flow control device is in a sufficiently open or closed position, wherein the feedback mechanism is an auditory feedback mechanism.

20. The system of claim 13, wherein the fluid flow control device further comprises a sealing mechanism configured to create a seal in a space between the external casing and the internal casing and prevent leakage of fluid from the device.

* * * * *